United States Patent [19]
Nakanishi et al.

[11] 3,932,325
[45] Jan. 13, 1976

[54] PROCESS FOR PREPARING 6-CHLORO-2-CHLOROMETHYL-4-PHENYLQUINAZOLINE-3-OXIDE AND INTERMEDIATES THEREFOR

[75] Inventors: Susumu Nakanishi, Niantic; Wayne E. Barth, East Lyme, both of Conn.

[73] Assignee: Pfizer Inc., New York, N.Y.

[22] Filed: Sept. 23, 1974

[21] Appl. No.: 508,103

[52] U.S. Cl. ....... 260/251 Q; 260/562 B; 260/566 D
[51] Int. Cl.² ..................................... C07D 239/76
[58] Field of Search ................................ 260/251 Q

[56] References Cited
UNITED STATES PATENTS
3,340,253  9/1967  Reeder et al. .................... 260/239.3

Primary Examiner—Raymond V. Rush
Attorney, Agent, or Firm—Connolly and Hutz

[57] ABSTRACT

A process is described for the preparation of 6-chloro-2-chloromethyl-4-phenylquinazoline-3-oxide, a key intermediate in the synthesis of the known useful psychotherapeutic agents: chlorodiazepoxide and diazepam. This intermediate is prepared by the cyclization of 2-(1′-chloroimino-2′-chloromethyl)-5-chlorobenzophenone, itself a new compound. This compound in turn is prepared by the chloroacetylation of 2-amino-5-chlorobenzophenone to 2-chloroacetamido-5-chlorobenzophenone, another novel compound, and subsequent iminochloride formation.

1 Claim, No Drawings

PROCESS FOR PREPARING 6-CHLORO-2-CHLOROMETHYL-4-PHENYL-QUINAZOLINE-3-OXIDE AND INTERMEDIATES THEREFOR

BACKGROUND OF THE INVENTION

The 1,4-benzodiazepine 4-oxides: 7-chloro-2-methylamino-5-phenyl-3H-1,4-benzodiazepine 4-oxide (chlorodiazepoxide) and 7-chloro-1,3-dihydro-1-methyl-5-phenyl-2H-1,4-benzodiazepin-2-one (diazepam); have found wide clinical acceptance in the treatment of psychoneurotic states manifested by tension, anxiety, apprehension, fatigue, depression, agitation and acute alcohol withdrawal. The preparation of these compounds and intermediates therefor are described, for example, in U.S. Pat. Nos. 2,893,992; 3,311,612; 3,446,806; 3,340,253; 3,102,116; 3,109,843 and 3,136,815.

SUMMARY OF THE INVENTION

This invention is concerned with a process for preparing 6-chloro-2-chloromethyl-4-phenylquinazoline, a key intermediate in the synthesis of the known useful psychotherapeutic agents: chlorodiazepoxide and diazepam. This intermediate is prepared by the cyclization of 2-(1'-chloroimino-2'-chloromethyl)-5-chlorobenzophenone which in turn is prepared by the chloroacetylation of 2-amino-5-chlorobenzophenone to 2-chloroacetamido-5-chlorobenzophenone and subsequent iminochloride formation.

DETAILED DESCRIPTION OF THE INVENTION

A known process for the preparation of 7-chloro-2-methylamino-5-phenyl-3H-1,4-benzodiazepine 4-oxide (chlorodiazepoxide) and 7-chloro-1,3-dihydro-1-methyl-5-phenyl-2H-1,4-benzodiazepin-2-one (diazepam) involves the use of the important intermediate, 6-chloro-2-chloromethyl-4-phenylquinazoline-3-oxide. This compound, described in U.S. Pat. No. 2,893,992, is prepared by converting 2-amino-5-chlorobenzophenone to the oxime (α and β-oxime mixture) which is then treated with a mixture of hydrochloric and acetic acids to give the desired compound. This may be contacted with methylamine to yield chlorodiazepoxide or in a series of steps to give diazepam.

The process of the present invention is concerned with an alternate route to the preparation of 6-chloro-2-chloromethyl-4-phenylquinazoline-3-oxide which involves the use of the new intermediates, 2-chloroacetamido-5-chlorobenzophenone and 2-(1'-chloroimino-2'-chloromethyl)-5-chlorobenzophenone. This improved process, obviating the troublesome mixture of the oximes of 2-amino-5-chlorobenzophenone referred to above, proceeds smoothly to give the desired intermediate compound in high yield.

In the process of the present invention, 2-amino-5-chlorobenzophenone is chloroacetylated to yield 2-chloroacetamido-5-chlorobenzophenone. Subsequent iminochloride formation leads to 2-(1'-chloroimino-2'-chloromethyl)-5-chlorobenzophenone. Cyclization of this compound yields 6-chloro-2-chloromethyl-4-phenylquinazoline-3-oxide.

The overall synthetic outline is as follows:

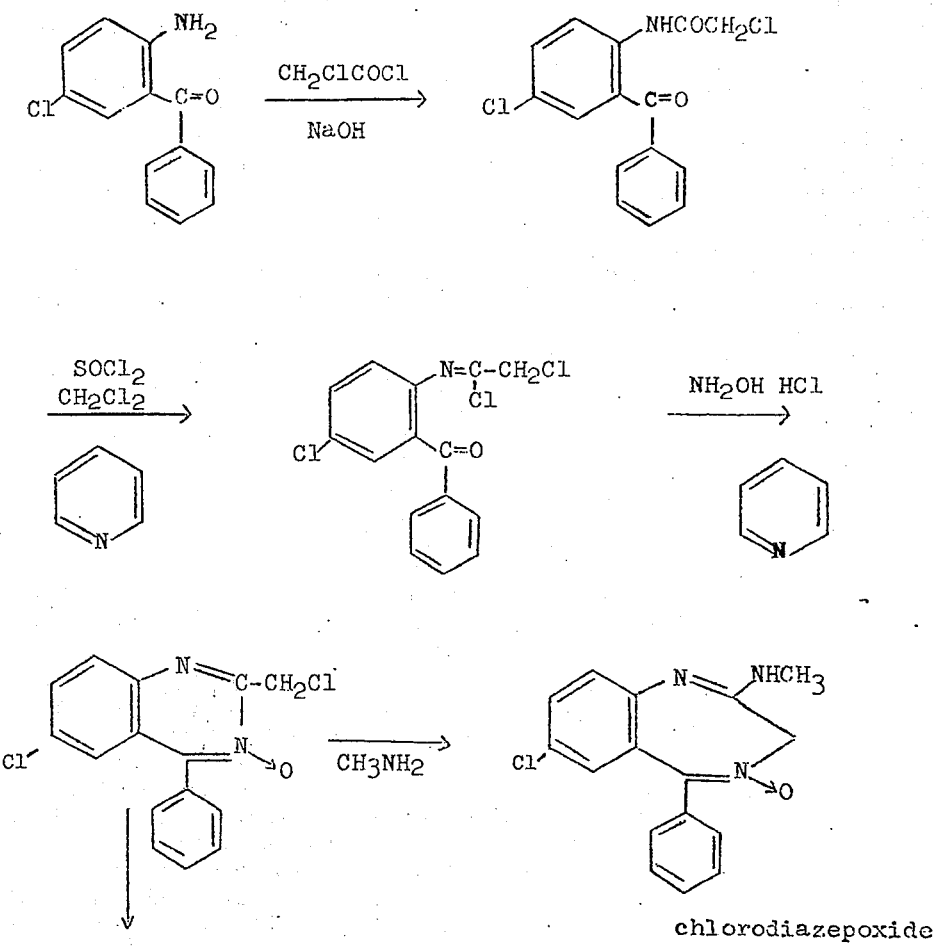

chlorodiazepoxide

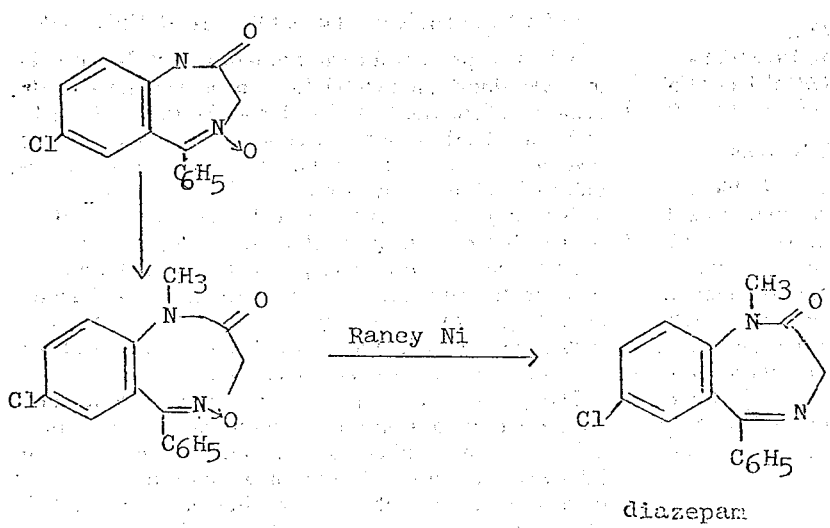

diazepam

2-Chloroacetamido-5-chlorobenzophenone is prepared by stirring under nitrogen a solution of 2-amino-5-chlorobenzophenone in an organic solvent such as benzene, methylene chloride, chloroform or the preferred solvent ethyl acetate with a slight molar excess of 3 N NaOH aqueous solution maintained at a temperature of about 5° to 25°C., preferably about 15°C. This is followed by the dropwise addition of a slight molar excess of chloroacetyl chloride during a period of about 15 minutes, maintaining the reaction temperature at 15°–25°C. The reaction time is from 1 to 4 hours with the reaction substantially complete in about 1.5 hours.

In a preferred process, 2-chloroacetamido-5-chlorobenzophenone dissolved in methylene chloride is contacted at room temperature under nitrogen with about 1.5 to 2 molar equivalents of thionyl chloride and about 3 molar equivalents of pyridine. The stirred mixture is then heated under gentle reflux for about 18 to 20 hours at 40°–42°C. In place of methylene chloride, chloroform at a reaction temperature of about 60°C. or benzene at 80°C. may be used. Phosgene or phosphorus pentachloride may be used in place of thionyl chloride.

To the crude methylene chloride solution of 2-(1′-chloroimino-2′-chloromethyl)-5-chlorobenzophenone, obtained as described above, is added a slight molar excess of hydroxylamine hydrochloride followed by 2–3 molar equivalents of pyridine. The solution is stirred at 25°–40°C. until the reaction is substantially complete (20–48 hours). In place of methylene chloride, chloroform at a reaction temperature of about 60°C. or benzene at 80°C. may be used. 6-Chloro-2-chloromethyl-4-quinazoline-3-oxide may be isolated as such, if desired, from the resulting reaction mixture by pouring said mixture into an ice-water solution of sodium carbonate, and concentrating the separated methylene chloride layer. Alternatively, the compound may be isolated as the hydrochloride by pouring the reaction mixture into ice-water, and working up the separated methylene chloride layer.

The intermediate, 6-chloro-2-chloromethyl-4-phenylquinazoline-3-oxide, may be converted to the known useful psychotherapeutic agents, chlorodiazepoxide and diazepam, by reported procedures is illustrated in the above synthetic outline and more specifically in the aforementioned patents.

EXAMPLE I

Preparation of 2-chloroacetamido-5-chlorobenzophenone

Under nitrogen atmosphere, a stirred solution of 23.17 g (0.1 mole) of 2-amino-5-chlorobenzophenone in 200 ml of ethyl acetate was cooled to 15°C. Then with ice-water bath cooling, 36.7 ml (0.11 mole) of 3 N NaOH aqueous solution was added keeping the temperature between 15° and 20°C. followed by the dropwise addition of 8.76 ml (0.11 mole) of chloroacetyl chloride during a period of 15 minutes maintaining the reaction temperature at 15°–25°C. When the addition of chloroacetyl chloride was completed, a mass of solid appeared. The slurry was stirred at 20°–23°C. for about 1.5 hours.

The solid was removed by filtration and washed with 100 ml of ethyl acetate. The combined clear ethyl acetate solution was then concentrated to about one-half volume, and the ethyl acetate replaced with n-heptane. The white crystalline material obtained was collected by filtration, washed with n-heptane and dried to constant weight to give 29.5 g of 2-chloroacetamido-5-chlorobenzophenone (96% of theory), m.p. 119°–120°C.

Analysis. Calcd. for $C_{15}H_{11}NO_2Cl_2$ (percent): C, 58.46; H, 3.60; N, 4.54; Cl, 23.01.

Found (percent): C, 58.62; H, 3.59; N, 4.45; Cl, 23.80.

EXAMPLE II

Preparation of 2-(1′-chloroimino-2′-chloromethyl)-5-chlorobenzophenone

Under nitrogen atmosphere, 5 g (16.2 m. moles) of 2-chloroacetamido-5-chlorobenzophenone was dissolved in 100 ml of methylene chloride. To this solution at room temperature was added 1.77 ml (24.3 m. moles) of thionyl chloride followed by 3.92 ml (48.6 m. moles) of pyridine. The stirred mixture was heated under gentle reflux at 40° ± 2°C. for 18 hours. Iminochloride formation was demonstrated by n.m.r., namely, chemical shift of $CH_2Cl$ from 4.11 ppm ($\delta$) to 5.17 ppm ($\delta$); NH doublet at 8.6 and 8.8 ppm ($\delta$) peaks had disappeared.

The methylene chloride solution of crude iminochloride was used directly in the next step reaction without isolation.

EXAMPLE III

Preparation of 6-chloro-2-chloromethyl-4-phenylquinazoline-3-oxide

To the crude methylene chloride solution of iminochloride obtained in Example II (assumed 100% of iminochloride or 16.2 m. moles) was added at room temperature (24°C.) 1.237 g (1.1 equiv., 17.8 m. moles) of hydroxylamine hydrochloride followed by 2.88 ml (2.2 equiv.) of pyridine. The reaction mixture was stirred at room temperature for 48 hours. The reaction mixture was then poured into ice-water containing 5.15 g of sodium carbonate (3 equiv., 48.6 m. moles). The separated methylene chloride layer was washed with water, dried over anhydrous magnesium sulfate and filtered. The solution was concentrated to about one-half volume, and the methylene chloride replaced with n-hexane. The formed crystalline material was granulated in hexane, collected by filtration, washed with hexane and dried to give 3 g (60.6%) of 6-chloro-2-chloromethyl-4-phenylquinazoline-3-oxide, m.p. 132°–134°C.

Analysis. Calcd. for $C_{15}H_{10}NO_2Cl_2$ (percent): C, 59.03; H, 3.30; N, 9.18 Cl, 23.24.

Found (percent): C, 59.23, H, 3.64; N, 9.37; Cl, 23.26.

The 6-chloro-2-chloromethyl-4-phenylquinazoline-3-oxide may be isolated, if desired, as the hydrochloride, m.p. 112°–122°C. (dec.) by pouring the reaction mixture as described above into ice-water (without added sodium carbonate) and working up the separated methylene chloride solution.

What is claimed is:

1. A process for preparing 6-chloro-2-chloromethyl-4-phenylquinazoline-3-oxide which comprises the steps of
   a. adding chloroacetyl chloride to a solution under nitrogen atmosphere of 2-amino-5-chlorobenzophenone in methylene chloride, chloroform, benzene or ethyl acetate and 3 N NaOH solution and stirring at 5°–25°C for about 1–4 hours;
   b. separating and contacting the resulting 2-chloroacetamido-5-chlorobenzophenone of step (a) in methylene chloride, chloroform or benzene solvent solution with thionyl chloride, phosgene or phosphorus pentachloride in pyridine under nitrogen atmosphere and heating under reflux; and
   c. contacting the resulting crude methylene chloride, chloroform or benzene solvent solution of 2-(1'-chloroimino-2'-chloromethyl)-5-chlorobenzophenone of step (b) with hydroxylamine hydrochloride and pyridine, stirring at 25°–80°C, pouring reaction mixture into ice-water solution of sodium carbonate, drying the resulting separated methylene chloride, chloroform or benzene layer, concentrating and replacing the methylene chloride, chloroform or benzene with hexane, and collecting formed crystalline 6-chloro-2-chloromethyl-4-phenylquinazoline-3-oxide.

* * * * *